(12) United States Patent
Schramm et al.

(10) Patent No.: US 7,610,118 B2
(45) Date of Patent: Oct. 27, 2009

(54) DISPENSING OF MULTIPLE VOLATILE SUBSTANCES

(75) Inventors: Heather R. Schramm, Whitewater, WI (US); Scott D. Walter, Twin Lakes, WI (US); Thomas Jaworski, Racine, WI (US); Thomas A. Helf, New Berlin, WI (US); Jose Porchia, Greenfield, WI (US); Edward J. Martens, III, Racine, WI (US); David A. Tomkins, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 181 days.

(21) Appl. No.: 10/549,435

(22) PCT Filed: Nov. 10, 2003

(86) PCT No.: PCT/US03/36090

§ 371 (c)(1),
(2), (4) Date: Sep. 15, 2005

(87) PCT Pub. No.: WO2004/043502

PCT Pub. Date: May 27, 2004

(65) Prior Publication Data

US 2006/0175426 A1    Aug. 10, 2006

(51) Int. Cl.
*G05D 11/00* (2006.01)
(52) U.S. Cl. .................. 700/283; 239/69; 261/20
(58) Field of Classification Search ............ 700/231, 700/239–241, 265, 281–284; 422/5, 105; 222/25, 52, 54, 145.5, 145.6; 239/34, 69; 261/19, 20, 26
See application file for complete search history.

(56) References Cited

U.S. PATENT DOCUMENTS

| | | | |
|---|---|---|---|
| 2,103,609 A | 12/1937 | Bradburn |
| 2,555,047 A | 5/1951 | Logue |
| 2,608,436 A | 8/1952 | Baughman |
| 3,410,488 A | 11/1968 | Sugimura |
| 3,711,023 A | 1/1973 | Smith |
| 4,346,059 A | 8/1982 | Spector |
| 4,556,539 A | 12/1985 | Spector |
| 4,603,030 A | 7/1986 | McCarthy |
| 4,629,604 A | 12/1986 | Spector |
| 4,695,434 A | 9/1987 | Spector |
| 4,804,821 A | 2/1989 | Glucksman |
| 5,011,632 A | 4/1991 | Yano et al. |
| 5,023,020 A | 6/1991 | Machida et al. |
| 5,050,798 A | 9/1991 | Sullivan |

(Continued)

FOREIGN PATENT DOCUMENTS

CA     2222838     1/1997

(Continued)

*Primary Examiner*—Charles R Kasenge

(57) ABSTRACT

A method and apparatus for controlling emission of fragrances into a given area such as a room or a region of a yard; and more particularly the creation of a desired atmosphere within the given area. In addition, the invention involves a volatile substance dispensing device (200) having mounted therein a plurality of reservoirs (31) storing a volatile substance, and a plurality of atomizer assemblies (34) for emitting volatile substances communicated thereto by the reservoirs (31). Preferably, a microcontroller (50) controls the emission of the volatile substances in accordance with preferred programs.

33 Claims, 13 Drawing Sheets

U.S. PATENT DOCUMENTS

| | | | |
|---|---|---|---|
| 5,071,621 A | 12/1991 | Tokuhiro et al. | |
| 5,105,133 A | 4/1992 | Yang | |
| 5,111,477 A | 5/1992 | Muderlak | |
| 5,115,975 A | 5/1992 | Schilling | |
| 5,163,616 A | 11/1992 | Bernarducci et al. | |
| 5,167,877 A | 12/1992 | Pai | |
| 5,175,791 A | 12/1992 | Muderlak et al. | |
| 5,178,327 A | 1/1993 | Palamand et al. | |
| 5,234,162 A | 8/1993 | Sullivan | |
| 5,342,584 A | 8/1994 | Fritz et al. | |
| RE34,847 E | 2/1995 | Muderlak et al. | |
| 5,402,517 A | 3/1995 | Gillett et al. | |
| D359,346 S | 6/1995 | Martin | |
| 5,565,148 A | 10/1996 | Pendergrass, Jr. | |
| 5,591,409 A | 1/1997 | Watkins | |
| 5,647,052 A | 7/1997 | Patel et al. | |
| 5,658,387 A | 8/1997 | Reardon et al. | |
| 5,666,186 A * | 9/1997 | Meyerhoefer et al. | 396/281 |
| 5,695,692 A | 12/1997 | Kennedy | |
| 5,724,256 A | 3/1998 | Lee et al. | |
| 5,734,590 A | 3/1998 | Tebbe | |
| 5,805,768 A | 9/1998 | Schwartz et al. | |
| 5,884,808 A | 3/1999 | Muderlak et al. | |
| 5,887,118 A * | 3/1999 | Huffman et al. | 392/390 |
| 5,972,290 A | 10/1999 | DeSousa | |
| 6,039,212 A * | 3/2000 | Singh | 222/54 |
| 6,044,202 A | 3/2000 | Junkel | |
| 6,053,738 A | 4/2000 | Ivey, Jr. | |
| 6,136,277 A | 10/2000 | Nardini | |
| 6,196,218 B1 | 3/2001 | Voges | |
| 6,241,944 B1 | 6/2001 | Budman | |
| 6,254,065 B1 | 7/2001 | Ehrensperger et al. | |
| 6,282,458 B1 * | 8/2001 | Murayama et al. | 700/239 |
| 6,338,818 B2 | 1/2002 | Budman | |
| 6,357,726 B1 | 3/2002 | Watkins | |
| 6,371,451 B1 | 4/2002 | Choi | |
| 6,379,242 B1 * | 4/2002 | Wiseman et al. | 454/337 |
| 6,390,453 B1 | 5/2002 | Frederickson et al. | |
| 6,406,004 B1 | 6/2002 | Ude | |
| D463,437 S | 9/2002 | Bush et al. | |
| 6,446,583 B2 | 9/2002 | Vieira | |
| D464,130 S | 10/2002 | Denham et al. | |
| 6,487,367 B2 | 11/2002 | Vieira | |
| 6,501,906 B2 | 12/2002 | Vieira | |
| 6,502,762 B2 | 1/2003 | Tuttobene, Jr. | |
| 6,511,531 B1 | 1/2003 | Cartellone | |
| 6,536,746 B2 | 3/2003 | Watkins | |
| 6,542,442 B2 | 4/2003 | Kaslon | |
| 6,554,203 B2 | 4/2003 | Hess et al. | |
| 6,556,272 B1 * | 4/2003 | Du et al. | 352/85 |
| 6,563,091 B2 | 5/2003 | Vieira | |
| 6,568,659 B2 | 5/2003 | Hugon | |
| 6,569,387 B1 | 5/2003 | Furner et al. | |
| 6,581,915 B2 * | 6/2003 | Bartsch et al. | 261/26 |
| 6,592,104 B2 | 7/2003 | Cox | |
| 6,602,475 B1 | 8/2003 | Chiao | |
| 6,615,881 B2 * | 9/2003 | Bartholomew et al. | 222/144 |
| 6,619,559 B2 | 9/2003 | Wohrle | |
| 6,623,785 B2 * | 9/2003 | Childers | 427/2.14 |
| 6,661,967 B2 | 12/2003 | Levine et al. | |
| 6,712,287 B1 | 3/2004 | Le Pesant et al. | |
| 6,713,024 B1 | 3/2004 | Arnell et al. | |
| 6,714,725 B2 | 3/2004 | Grone et al. | |
| 6,728,478 B2 | 4/2004 | Cox et al. | |
| 6,739,479 B2 * | 5/2004 | Contadini et al. | 222/52 |
| 6,766,651 B2 * | 7/2004 | Dillenback | 222/1 |
| 6,790,408 B2 | 9/2004 | Whitby et al. | |
| 6,792,199 B2 | 9/2004 | Levine et al. | |
| 6,802,460 B2 | 10/2004 | Hess et al. | |
| 6,803,987 B2 | 10/2004 | Manne | |
| 6,810,204 B2 | 10/2004 | Grone et al. | |
| 6,834,847 B2 | 12/2004 | Bush et al. | |
| 7,152,758 B2 * | 12/2006 | Fazzio et al. | 222/52 |
| 2002/0018181 A1 | 2/2002 | Manne | |
| 2002/0066798 A1 | 6/2002 | Laudamiel-Pellet et al. | |
| 2002/0068009 A1 | 6/2002 | Laudamiel-Pellet et al. | |
| 2002/0068010 A1 | 6/2002 | Laudamiel-Pellet et al. | |
| 2002/0158351 A1 | 10/2002 | Wohrle | |
| 2003/0088338 A1 * | 5/2003 | Phillips et al. | 700/282 |
| 2003/0102384 A1 | 6/2003 | Walter et al. | |
| 2003/0107139 A1 | 6/2003 | Wohrle | |
| 2003/0138241 A1 | 7/2003 | Pedrotti et al. | |
| 2003/0164557 A1 | 9/2003 | Chung et al. | |
| 2003/0168524 A1 | 9/2003 | Hess et al. | |
| 2003/0168751 A1 | 9/2003 | Bartsch et al. | |
| 2003/0175148 A1 | 9/2003 | Kvietok | |
| 2003/0192959 A1 | 10/2003 | Hess et al. | |
| 2003/0206834 A1 | 11/2003 | Chiao et al. | |
| 2003/0236451 A1 * | 12/2003 | El-Nokaly et al. | 600/300 |
| 2004/0007787 A1 | 1/2004 | Kvietok et al. | |
| 2004/0009103 A1 | 1/2004 | Westring | |
| 2004/0016818 A1 | 1/2004 | Murdell et al. | |
| 2004/0028551 A1 | 2/2004 | Kvietok et al. | |
| 2004/0033067 A1 | 2/2004 | He et al. | |
| 2004/0033171 A1 | 2/2004 | Kvietok et al. | |
| 2004/0071456 A1 | 4/2004 | Levine et al. | |
| 2004/0217188 A1 | 11/2004 | McEwen | |
| 2004/0223871 A1 | 11/2004 | Woo et al. | |
| 2004/0223943 A1 | 11/2004 | Woo et al. | |
| 2004/0241053 A1 | 12/2004 | Thompson et al. | |
| 2004/0247301 A1 | 12/2004 | Hagi et al. | |

FOREIGN PATENT DOCUMENTS

| | | |
|---|---|---|
| GB | 2418859 A | 4/2006 |
| WO | WO 00/12143 | 3/2000 |
| WO | WO 02/09772 A3 | 2/2002 |
| WO | WO 02/09773 A3 | 2/2002 |
| WO | WO 02/09776 A3 | 2/2002 |
| WO | WO 02/32472 A1 | 4/2002 |
| WO | WO 03/027220 A1 | 4/2002 |
| WO | WO 2004/093927 A1 | 11/2004 |
| WO | WO 2004/093928 A2 | 11/2004 |
| WO | WO 2004/093929 A2 | 11/2004 |
| WO | WO 2004/105813 A1 | 12/2004 |
| WO | WO 2004/105814 A1 | 12/2004 |
| WO | WO 2004/105815 A2 | 12/2004 |
| WO | WO 2004/105878 A1 | 12/2004 |

* cited by examiner

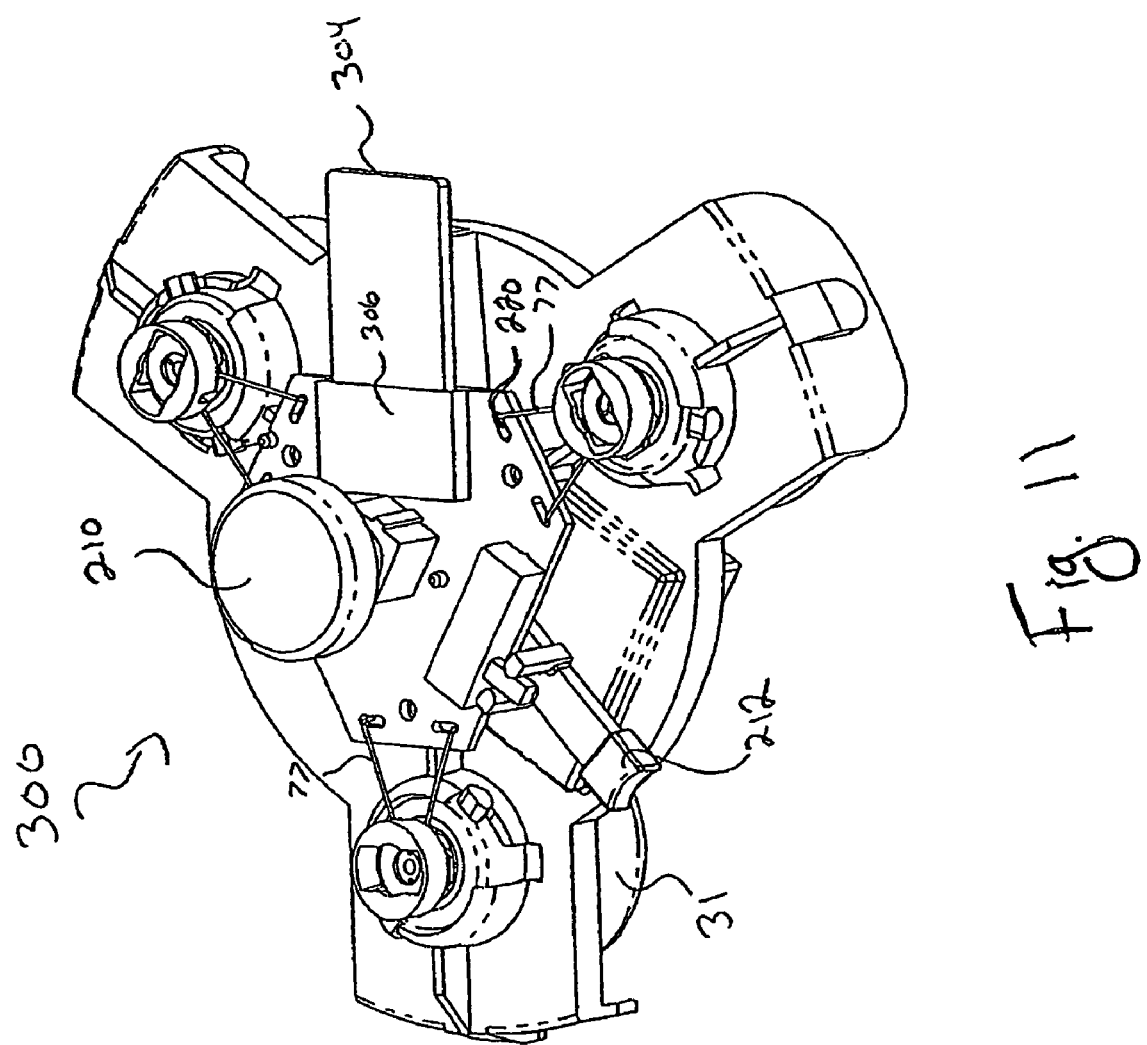

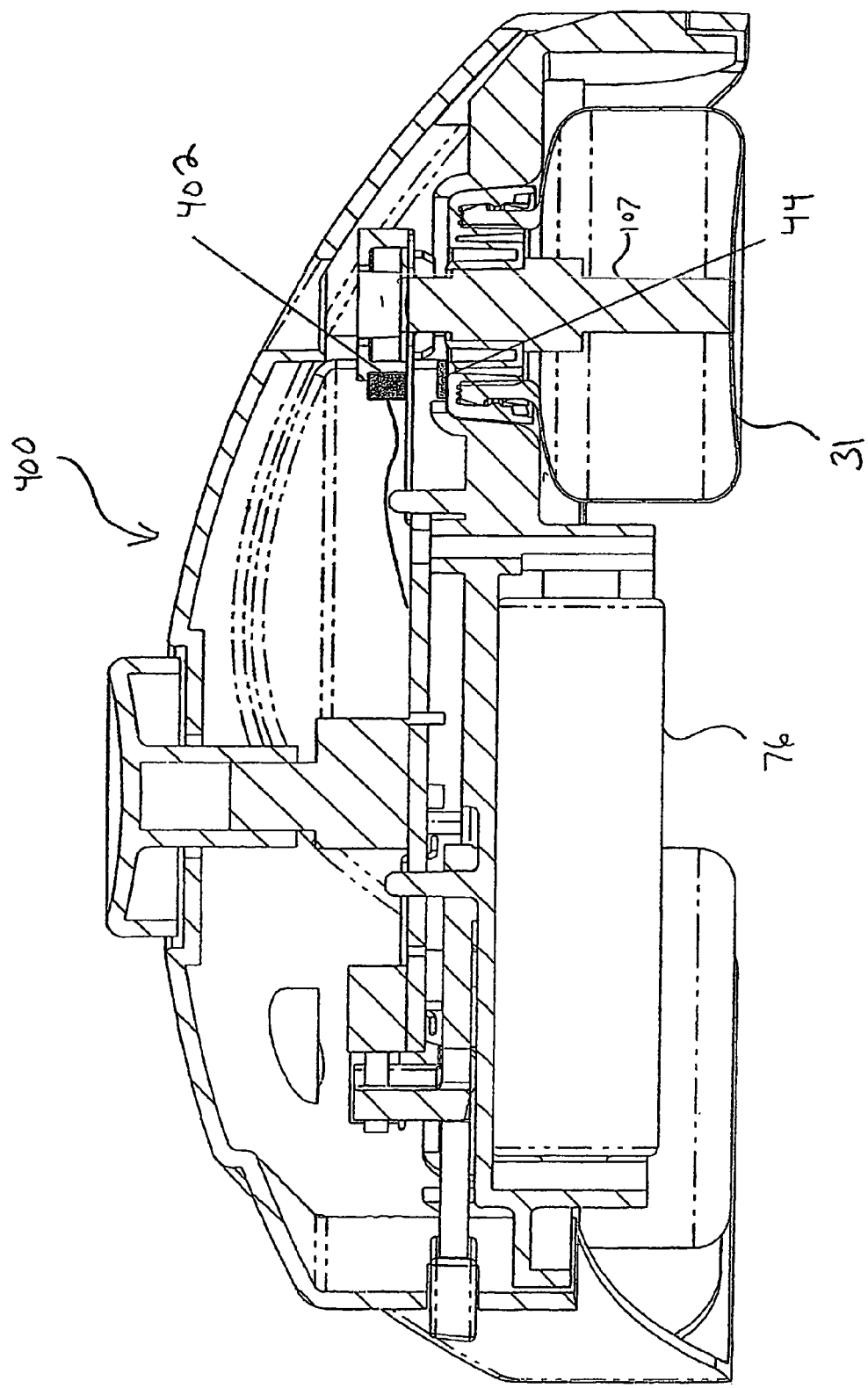

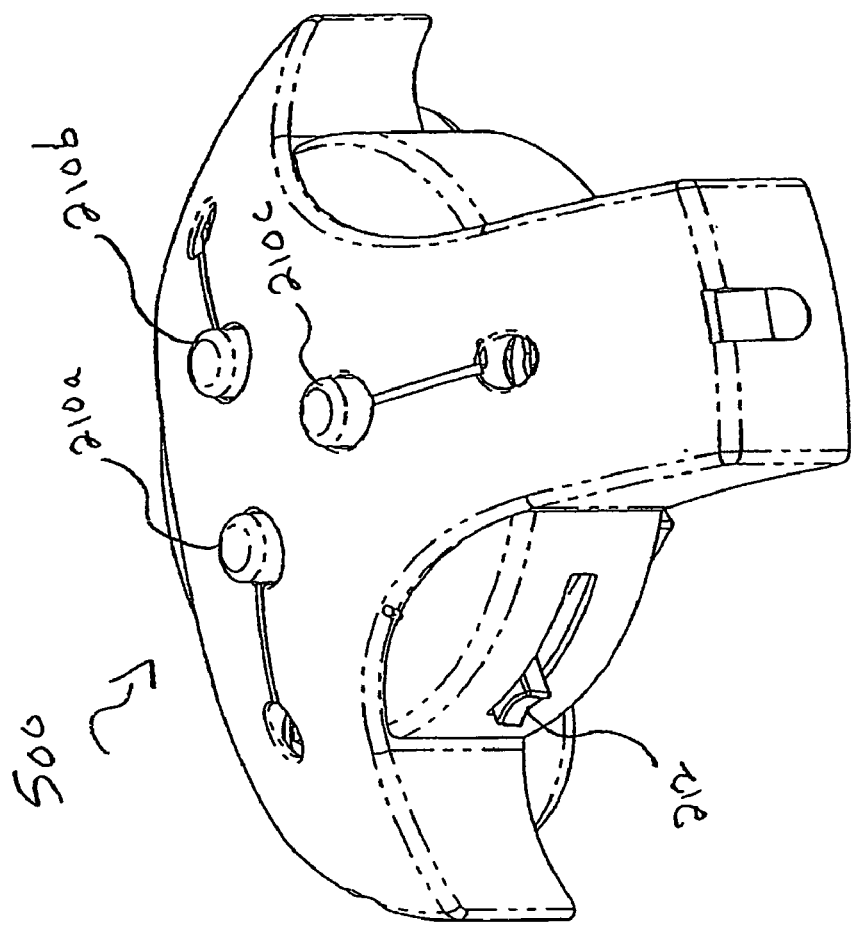

DISPENSING OF MULTIPLE VOLATILE SUBSTANCES

BACKGROUND OF THE INVENTION

1. Field of the Invention

Our invention relates to the controlled and coordinated emission of volatile substances (preferably fragrances and/or insecticides) into a given area such as a room or a region of a yard; and more particularly it concerns the creation of a desired atmosphere within the given area. In addition, our invention involves various means for providing instructions to a microcontroller/microprocessor to control the emission of volatile substances. Further, the emission of volatile substances, preferably fragrances, may be coordinated with the emission of light.

2. Description of the Related Art

There are known devices for controlling the atmosphere through the release of fragrance. U.S. Pat. No. 5,382,410 discloses an electrostatic vapor/aerosol generator for supplying aromatic oil, deodorant, disinfectant, fumigant, fungicide, insecticide or bactericide to a room. U.S. Pat. No. 4,702,418 discloses an adjustable aerosol dispenser for supplying different amounts of a fragrance into a room according to sensed light, odor, sound, etc., within the room. U.S. Pat. No. 5,115,975 discloses a device for emitting a vaporized substance, such as an insecticide, into the atmosphere according to the setting of a timer. U.S. Pat. No. 6,135,369 discloses an electrostatic sprayer which can spray insecticides, which can be controlled according to selected on times and off times, and which incorporates a sensor to sense the available power for continued operation. U.S. Pat. No. 4,689,515 discloses an ultrasonic liquid atomizer with automatic frequency control. U.S. Pat. No. 3,543,122 and No. 3,615,041 disclose aerosol dispensers having timers for controlling the operation of the dispensers according to preset times.

In addition, U.S. Pat. Nos. 5,591,409; 6,536,746; 6,241,944; and 6,136,277 describe the controlled release of fragrances from multiple dispensers.

The known fragrance delivery devices, however, are generally constructed independently and it is difficult to control the resultant overall effect when several of these devices are used in the same room or area. For those that do have centrally-controlled multiple dispensers provided in one housing, there is still a need for a more practical and efficient delivery system, effective control programs and mechanisms, and user-friendly operation.

Fragrance delivery may also be combined with lighting effects. Lighting devices which emit different colored light, such as from light emitting diodes (LED's) are known. Such devices may take the form of drop lights, candle lights or lamps, such as table lamps; and they may be battery operated or they may operate from power supplied by a wall outlet. These devices also may be controlled to emit different colored light, either upon the operation of a selection switch or automatically at different time intervals. In addition, such devices may be constructed to emit a scent to provide a desired ambience in a room.

Illumination arrangements which are controlled remotely are disclosed in U.S. Pat. Nos. 6,016,038, 6,150,774, 6,166,496, 6,211,626, 6,292,901 and 6,340,868. Also, the use of multiple light emitting diodes (LED's) in a single unit is disclosed in U.S. Pat. No. 6,149,283.

SUMMARY OF THE INVENTION

Our invention relates to the control of the emission of volatile substances, preferably using a microprocessor. The volatile substances may be any one of a number of substances including, but not limited to, water, fragrance, insecticide, insect repellant, air sanitizer, and disinfectant. Preferably, multiple fragrances are emitted in a controlled program from multiple fragrance dispensers.

According to one aspect of the invention, there are provided novel methods and apparatuses for producing desired ambient conditions in a given area such as a room or a yard. These novel methods and apparatuses involve a plurality of electrically controlled fragrance dispensers; and a controller which is constructed and connected to control the operation of the fragrance dispensers in a coordinated manner such that a desired combination of fragrance's emitted into the area. The controller is constructed and operated to cause the fragrance dispensers to emit fragrance in coordination with each other over a period of time. The controller may also control the emission of light and/or insecticide from a light emitting device and an insecticide dispenser, respectively.

In another aspect, the invention involves the use of a timer to control the coordinated operation of the fragrance dispensers and/or light emitting devices over a period of time according to a predetermined program. Further, other inputs may be used to control the operation of the dispensers. In particular, sensors may be provided that detect any one of light, motion, airborne chemicals, humidity, temperature, sound, etc.

In a preferred embodiment of our invention, a volatile substance dispensing system includes a plurality of electromechanical volatile substance dispensers, a programmable microprocessor, and a memory card reading device. The plurality of electromechanical dispensers are each configured to emit a volatile substance from a replaceable volatile substance reservoir when the reservoir is loaded in the dispensing system so as to communicate the volatile substance to each respective dispenser. The microprocessor controls the emission of different volatile substances from the plurality of dispensers. The memory card reading device reads programs from a replaceable memory card. The memory card comprises one or more programs for instructing the microprocessor to control volatile substance emission from the plurality of dispensers in a coordinated manner.

In another preferred embodiment of our invention, there is a method of selling replaceable volatile substance reservoirs for use in a volatile substance dispensing device. The dispensing device is configured to mount a plurality of volatile substance reservoirs simultaneously and to operate electromechanical dispensers to emit volatile substances from respective reservoirs independently or in combination. To achieve this, the dispensing device has a microprocessor and a memory card reading device for reading a memory card containing information relating to one or more computer-readable programs for instructing the microprocessor to control emission of fragrances from the fragrance reservoirs in accordance with the one or more programs. The method includes the steps of grouping a plurality of volatile substance reservoirs having a different volatile substance and storing on a memory card information relating to one or more programs for instructing the microprocessor to control the emission of the different volatile substances of the group. In addition, there are steps of packaging the plurality of reservoirs together with the memory card and offering the packaged materials for sale as a single item.

In yet another embodiment of our invention, there is a volatile substance dispensing system having a plurality of electromechanical volatile substance dispensers and a microprocessor. The plurality of electromechanical volatile substance dispensers are configured to dispense volatile substances from a plurality of replaceable volatile substance reservoirs, respectively, when the plurality of reservoirs are loaded in the dispensing system. The microprocessor controls the plurality of electromechanical dispensers to emit volatile substances from the plurality of reservoirs so as to perform at least one of (i) repetitive alternation between independent emissions of different volatile substances, (ii) repetitive alternation between emissions of different combinations of volatile substances, or (iii) repetitive alternation between different emission intensities of at least one volatile substance, in a set pattern.

In an additional embodiment of our invention, a volatile substance dispensing system includes a plurality of electromechanical volatile substance dispensers and a microprocessor. The plurality of electromechanical fragrance dispensers are each configured to dispense volatile substance from a replaceable volatile substance reservoir. (Each reservoir includes a wick that (i) extends into the reservoir, and (ii) communicates the volatile substance from the reservoir, through capillary action, to deliver the fragrance to the electromechanical dispenser.) Each electromechanical fragrance dispenser includes an orifice plate and a piezoelectric actuator element. The actuator element expands and contracts when alternating voltages are applied thereto. The expansion and contraction is communicated to the orifice plate to cause the orifice plate to vibrate and, consequently, to eject into the air droplets of a volatile substance communicated by the wick. The microprocessor controls the emission of volatile substances from the plurality of electromechanical dispensers by independently controlling the voltage applied to each actuator element.

In yet another preferred embodiment of our invention, a volatile substance dispensing system includes at least one electromechanical dispenser, at least one reading device, and a microprocessor. Each electromechanical dispenser is configured to dispense a volatile substance from a replaceable volatile substance reservoir when the reservoir is loaded in the volatile substance dispensing system. The reservoir includes information relating to the type of volatile substance contained therein. Each reading device reads the information from the reservoir relating to the type of volatile substance stored therein. The microprocessor controls the electromechanical dispenser to emit a volatile substance from the reservoir, with the microprocessor receiving one or more signals from the reading device relating to the information read from the reservoir. The microprocessor then controls the emission of a volatile substance from the reservoir based on the one or more signals received from the reading device.

In another preferred embodiment of our invention, a volatile substance dispensing system includes at least one electromechanical dispenser, at least one reading device, and a microprocessor. Each electromechanical dispenser is configured to dispense a volatile substance from at least one replaceable volatile substance reservoir, respectively, when the reservoir is loaded in the volatile substance dispensing system. In this embodiment, the reservoir includes information relating to one or more computer-readable programs. Each reading device reads the information from the fragrance reservoir. The microprocessor receives signals from the reading device communicating the information relating to one or more computer-readable programs and controls the at least one electromechanical dispenser to emit a volatile substance from the reservoir in accordance with the signals communicated from the reading device.

BRIEF DESCRIPTION OF THE DRAWINGS

FIG. 11 is a perspective view of the dispensing device shown in FIG. 10, with the top cover removed.

FIG. 12 is a cross-sectional view of yet another embodiment of a fragrance dispensing device according to our invention.

FIG. 13 is a perspective view of another embodiment of a fragrance dispensing device according to our invention.

DETAILED DESCRIPTION OF THE PREFERRED EMBODIMENT

General Configurations

Figure 1:
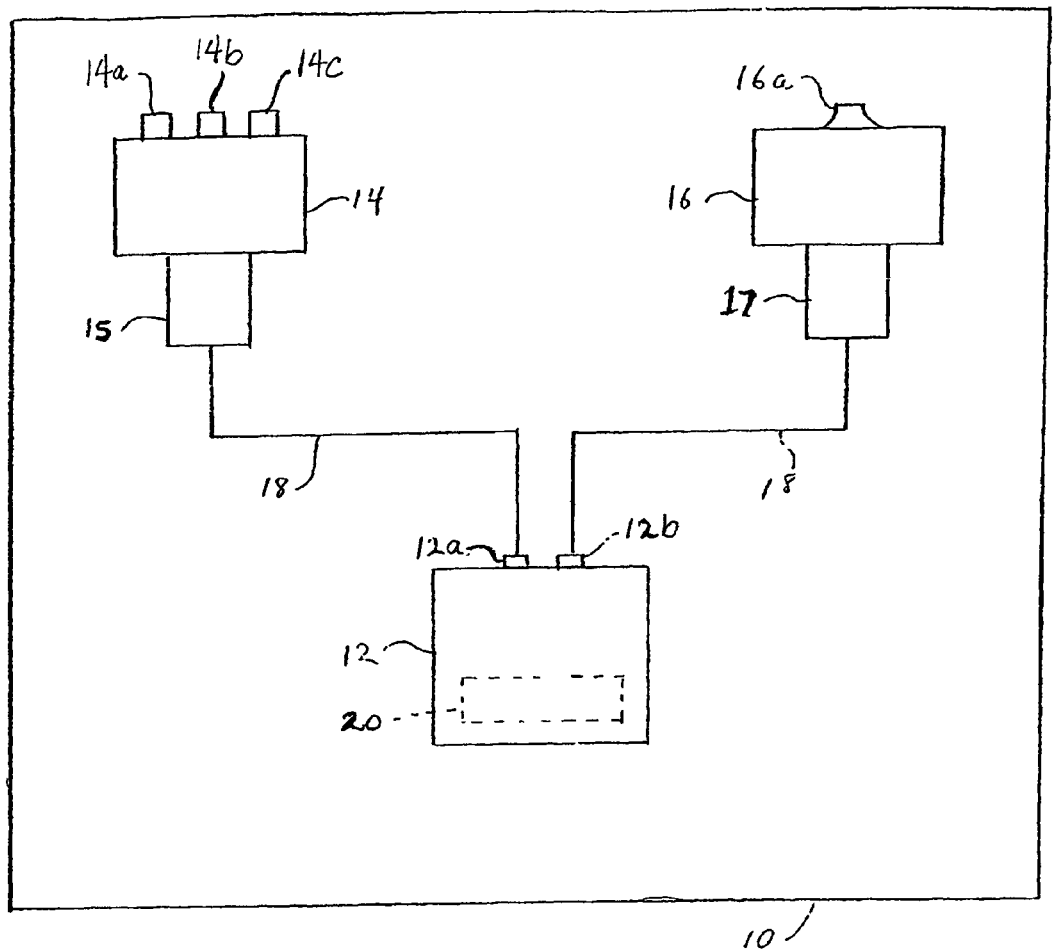
FIG. 1 is a diagrammatic plan view showing one embodiment of our invention.

As shown in FIG. 1, there is provided in a room 10, or other area such as a yard, a processor 12, a luminescent device 14 and a dispenser 16, for emitting a volatile substance (while any one of a number of volatile substances may be used, fragrances and insecticides will generally be discussed below for exemplary purposes). The luminescent device 14 is a light emitting device, and it may comprise a device that emits visible light or light for illumination. In a preferred arrangement, the luminescent device 14 includes light emitting diodes (LED's) 14a, 14b and 14c which emit light in different colors, respectively.

The dispenser 16 may be a mechanical atomization device such as shown and described in U.S. Pat. No. 6,292,196. In such a case, a fragrance (or insecticide), preferably, is supplied in liquid form to the dispenser and is atomized in the dispenser by any of various controllable means, for example, by an orifice plate that is vibrated by a piezoelectric actuator.

The processor 12 is a programmable device that produces output signals at terminals 12a and 12b according to an internal program. The output signals may be in the form of voltages or in the form of coded pulses or other coded signals which control the operation or output intensity of the luminescent device 14 and the fragrance or insecticide dispenser 16. The terminals 12a and 12b may be connected by means of wires 18 to control units 15 and 17 on the luminescent device 14 and the dispenser 16. Alternatively, the processor 12 may have a single output terminal connected via a common bus to the control units 15 and 17. In such a case, the coded signals are provided with appropriate addresses to ensure that they are recognized only by the particular control unit to which they are directed. It will also be appreciated that the wires 18 and the bus could be eliminated and the coded signals with addresses from the processor 12 could be transmitted to the control units 15 and 17 by wireless means such as by infra-red light or radio signals.

The processor 12 includes an internal clock 20 to control its operation according to a controlled program. In this manner, the luminescent device 14 and the dispenser 16 are controlled to emit light and fragrances in a coordinated manner over time into the area 10 to produce a desired effect within the area.

Figure 2:
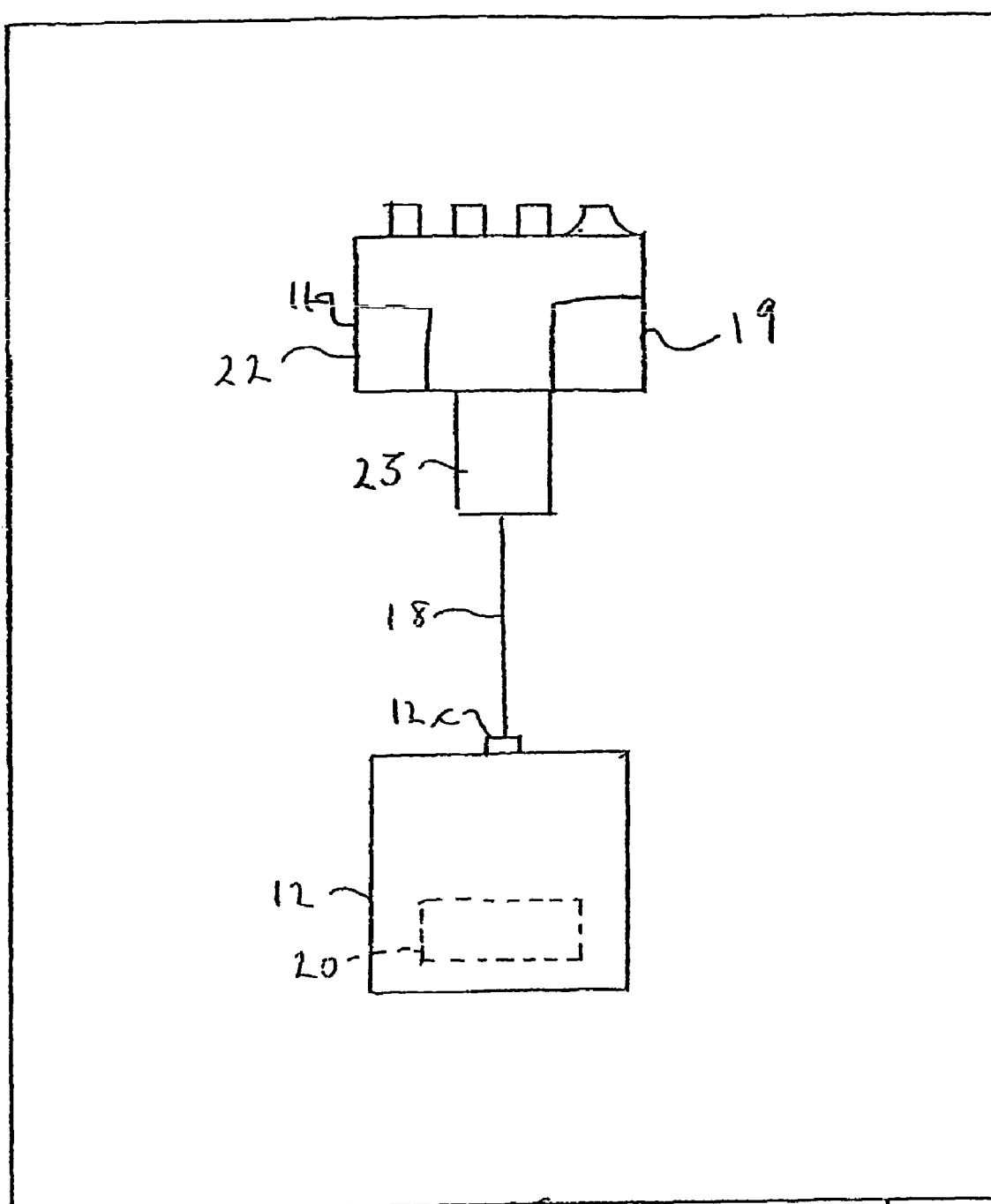
FIG. 2 is a diagrammatic plan view showing another embodiment of our invention.

FIG. 2 shows a modification of the invention in which the luminescent device 14 and the dispenser 16 are combined into a single integral unit 22. Here, signals at a terminal 12c are transmitted via a wire 18, or in a wireless manner, to a construction as in FIG. 1. The embodiment of FIG. 2 has the advantage that fewer devices are required and their set-up is simplified. In addition, as shown, a sensor 11 may be provided. Sensor 11 may provide information to the processor 12, which information may be used to control the integral unit 22. The sensed condition may be light intensity, temperature, sound, motion, humidity, air borne chemicals, etc.

Also as shown in FIG. 2, a continuous action dispenser 19 (e.g., a continuous action air freshener) may be provided in combination with integral unit 22. A continuous action dispenser is a dispenser that continually emits a volatile substance, although the rate of emission may be varied in some degree. The method of emission is typically evaporation of an exposed substance that readily evaporates from a liquid, solid or gel form, to slowly release the volatile substance over time. Such devices generally offer less control of the emission rate, and would preferably be used in connection with a dispenser such as a piezo-type dispenser that offers greater emission control. An example of such a dispenser may be found in U.S. Pat. No. 6,631,852.

Figure 3:
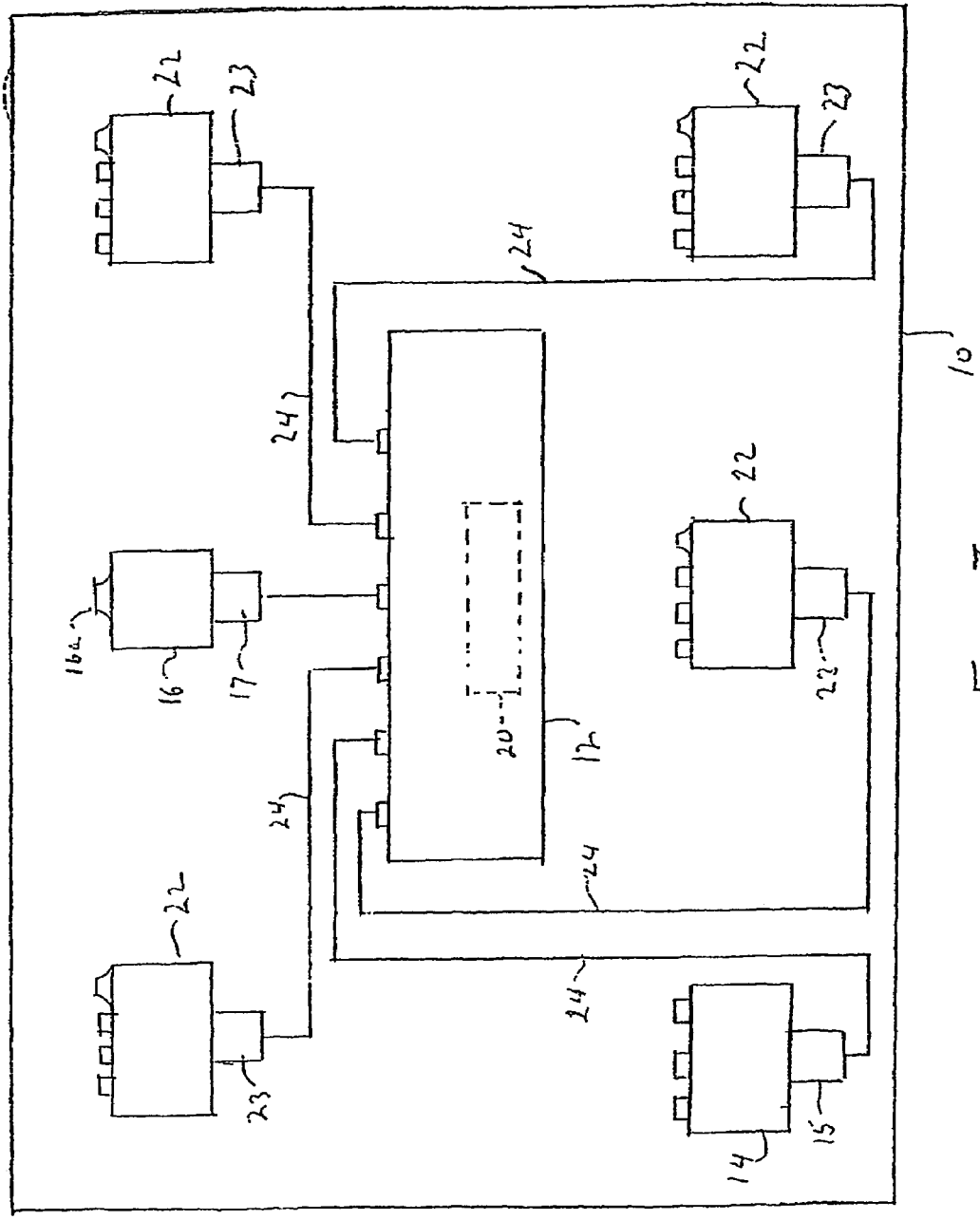
FIG. 3 is a diagrammatic plan view showing yet another embodiment of our invention.

FIG. 3 shows a third embodiment of the invention in which several luminescent devices 14 and dispensers 16 are provided and connected to be controlled in a controllable manner from a single processor 12. The embodiment of FIG. 3 may also, or alternatively, include combined luminescent devices and dispensers 22 of the type described in connection with FIG. 2. All of the devices are connected by means of wires 24 to the processor 12. Alternatively, the devices 14, 16 and 22 may communicate with the processor 12 by wireless means, such as radio, infrared or sound signals. The embodiment of FIG. 3 provides the advantage that a large area or multiple delivery systems to be provided in a single housing may be controlled by means of a single processor. Also, the processor 12 may be programmed to cause different effects to be produced in different parts of the area 10 or to combine fragrances in a single area.

The devices 14, 16 and 22 may be controlled from a common bus connected to the processor 12. In such a case, the processor 12 would be constructed to produce signals with appropriate addresses so as to control the output of desired ones of the devices 14, 16 and 22. Similarly, in the case where the signals are transmitted from the processor 12 to the devices 14, 16 and 22, such signals should be encoded with the address of the particular device to be controlled by the signals.

Dispensers for emitting fragrances are known in the art. As discussed, a variety of different types of dispensers may be used to construct our invention, including piezoelectrically actuated atomization devices, heat-assisted evaporation devices, fan-assisted evaporation devices, aerosol spray devices, lamps, and acoustical generators, among others. Even within each type of dispenser, variations are possible, as would be appreciated by one of ordinary skill in the art.

The preferred dispenser uses an atomizer that releases droplets of fragrance into the air. In such a case, a fragrance is supplied in liquid form to the dispenser and is atomized in the dispenser by any of various controllable means, for example, by an orifice plate that is vibrated by a piezoelectric actuator. Examples of mechanical atomization devices are shown and described in U.S. Pat. Nos. 6,296,196 and 6,341,732.

Figure 6:
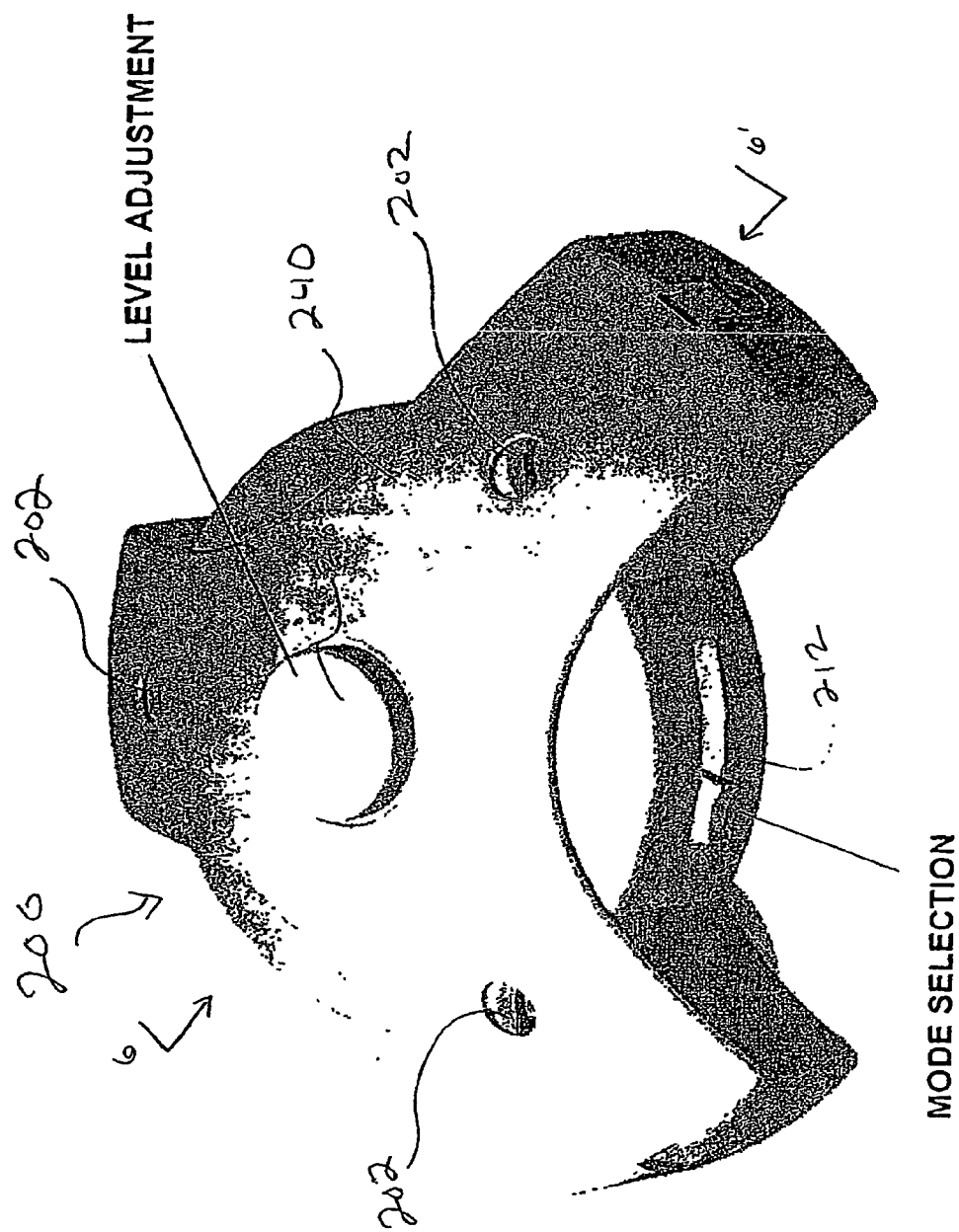
FIG. 6 is a perspective view of a fragrance dispensing system, with multiple fragrance dispensers.
Figure 7:
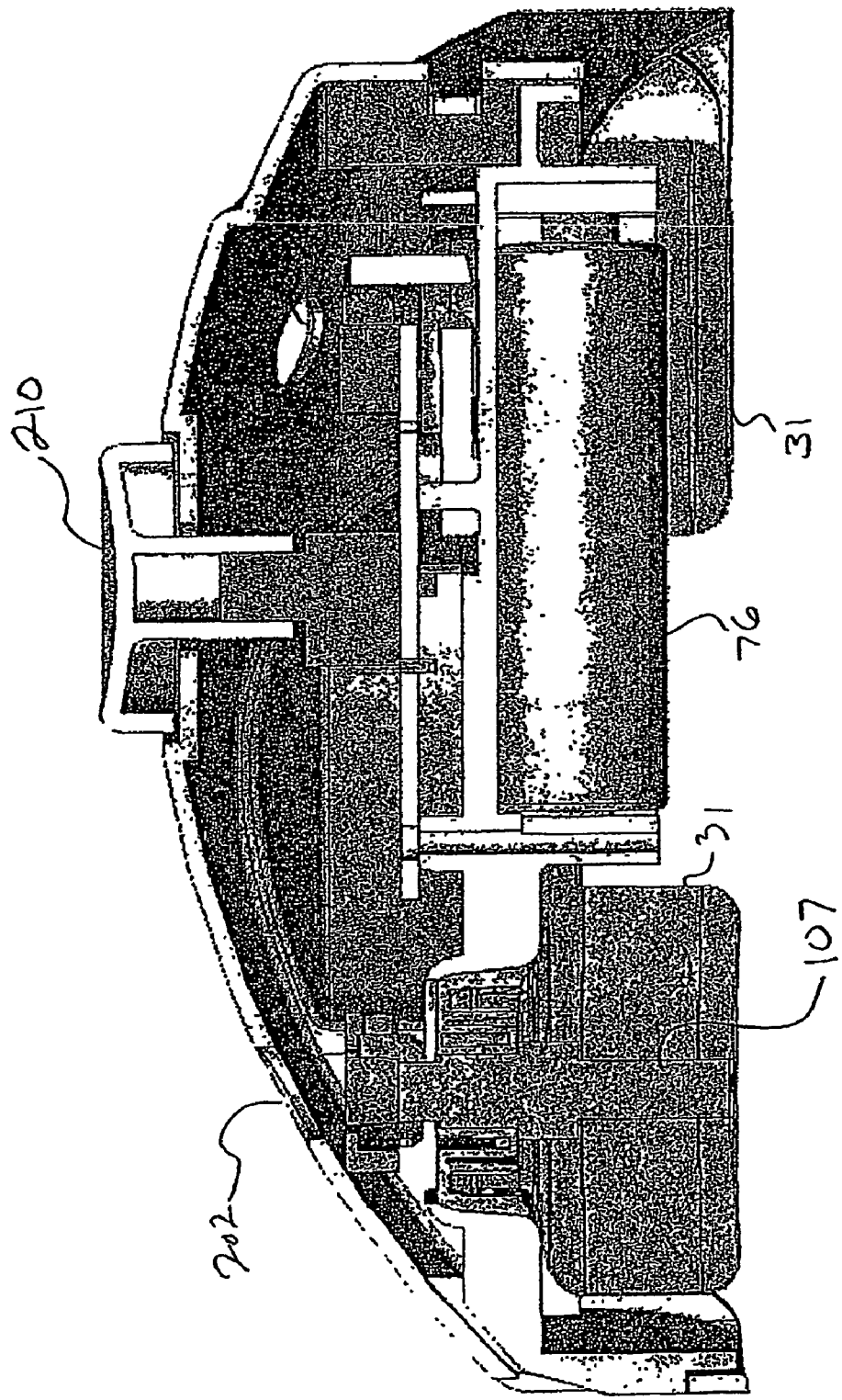
FIG. 7 is a partial cross-sectional view taken along line 6-6' in FIG. 6.
Figure 8:
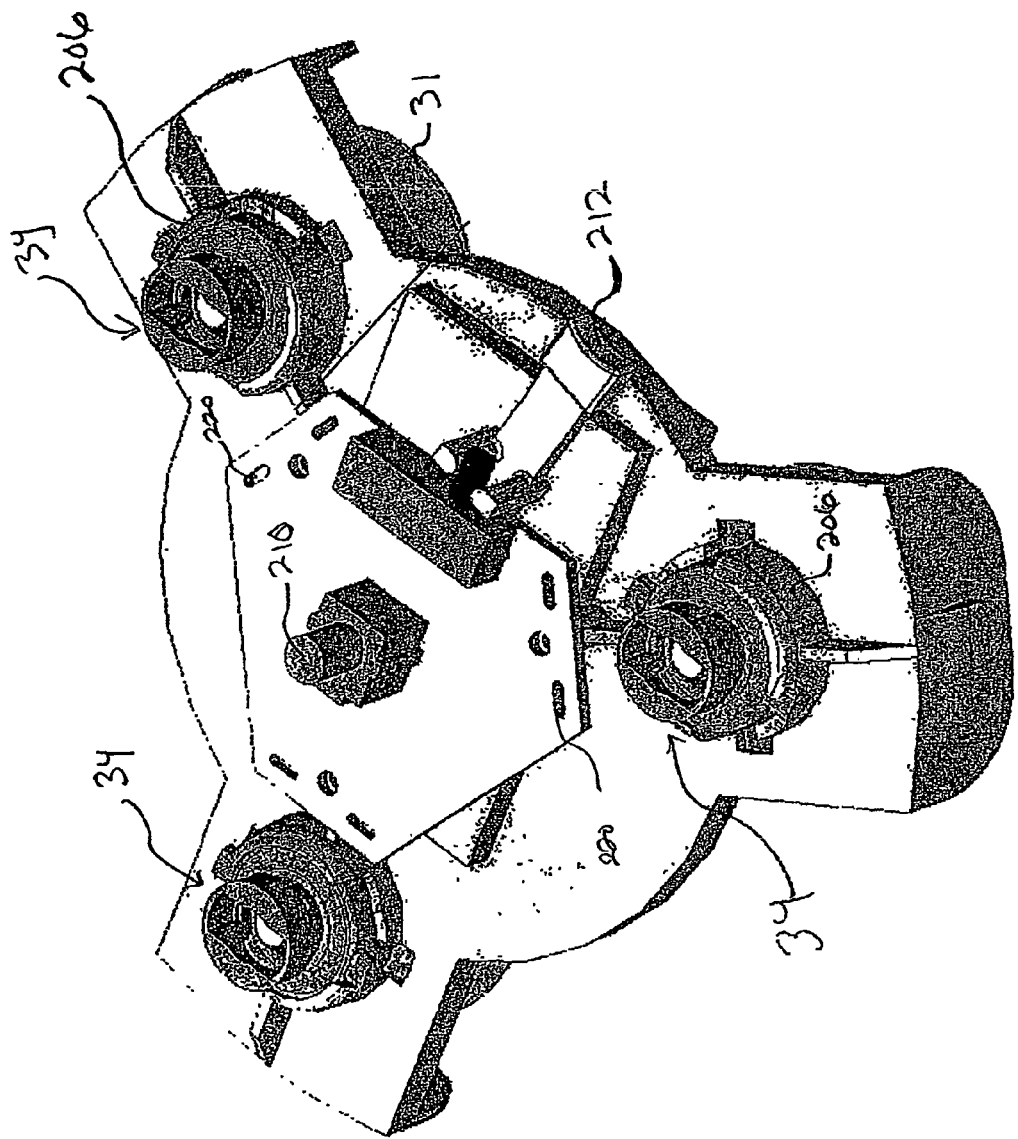
FIG. 8 a perspective view of the fragrance dispensing system shown in FIG. 6, with the top cover removed.

FIGS. 6-8 show a more preferred embodiment of our invention having three replaceable fragrance reservoirs 31 and three corresponding atomizer assemblies 34 (although other dispensers are possible) positioned in a single housing 200. Housing 200 includes three orifices 202 through which droplets of fragrance are emitted by atomizer assemblies 34. As discussed above, a single microprocessor may be provided to control the different atomizer assemblies 34. For a user interface, a knob 210 is provided for adjusting the level of fragrance to be emitted. Also, a mode lever 212 is provided to enable a user to switch between different emission modes (i.e., different programs for controlling emission from one or more of the reservoirs 31).

As shown in FIG. 8, when cover 240 is removed, fragrance reservoirs 31 can be positioned so as to be supported by collars 206, so that the reservoirs 31 are properly positioned for controlled emission using an actuator element (discussed below). Collars 206 ensure consistent positioning of replacement reservoirs with respect to the atomizer assemblies 34, so that the exposed wicks of the reservoirs engage the actuator elements. The wicks 107 use capillary action to communicate fragrance to the atomizer assembly 34. Collars 206 also allow other features of the reservoir to engage portions of the dispensing device 200. For instance, when the dispensing device 200 includes a reading device (discussed below) for reading information from a reservoir 31, collar 206, and corresponding mating features of the reservoir 31, can interlock to ensure that the information to be read is located proximately to the reading device. In other embodiments, other means may be provided for securing the reservoirs 31 in necessary positions for operating the fragrance dispensing system. These means may include slots formed to receive the bases of the reservoirs, clamps which provide a biasing force, male/female mating mechanisms, and the like. In this manner, the reservoirs can be easily mounted in or on housings by a user when the reservoirs are being replaced.

A plurality of openings 220 support wire-like supports 77 (shown in FIGS. 7 and 11). These wire-like structures support portions of the atomizer assembly 34, for instance, an actuator element, as discussed below with respect to FIG. 4, that mates with a reservoir 31.

Preferred Fragrance Dispenser

Figure 4:
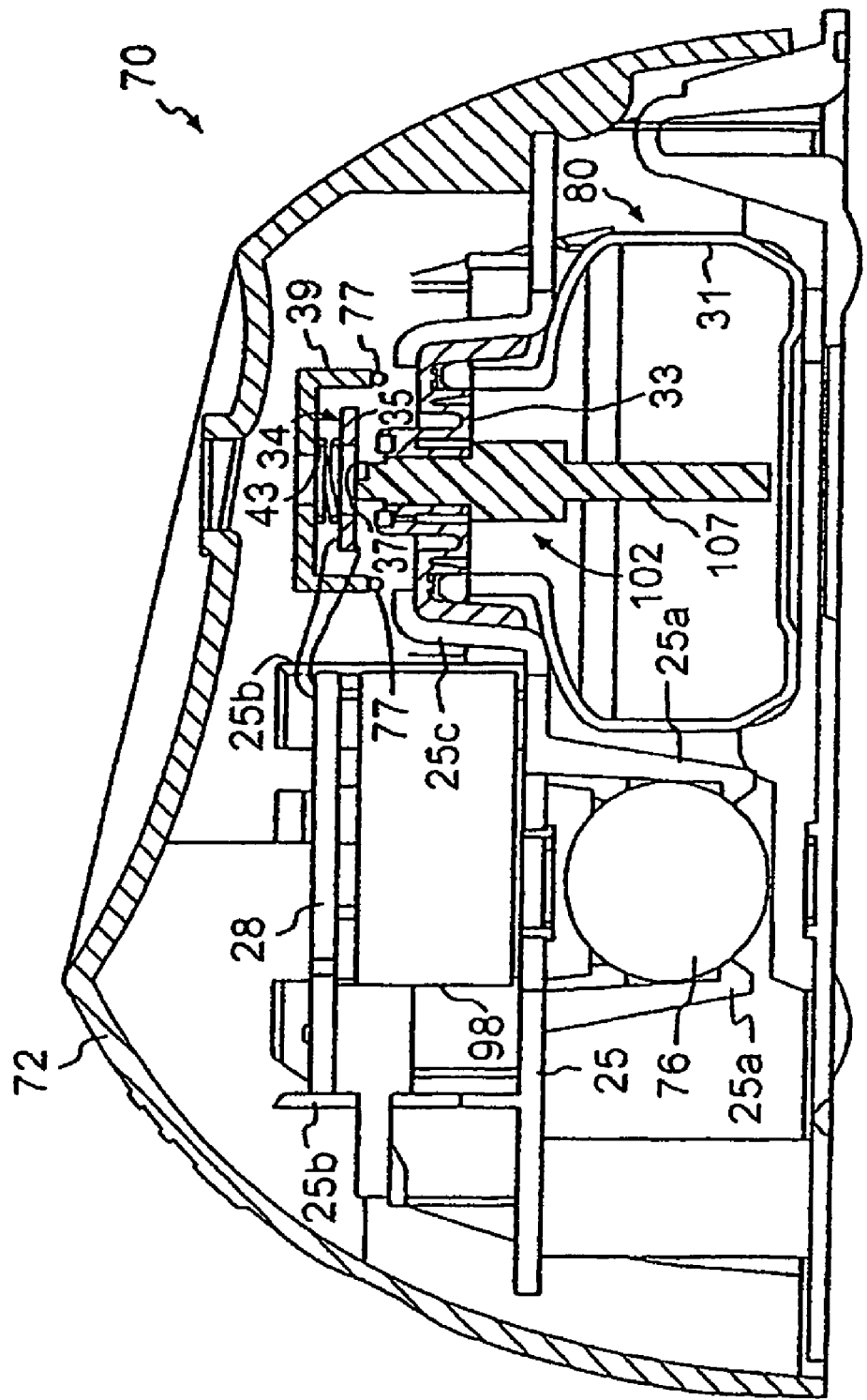
FIG. 4 is a cross-sectional view of a fragrance dispensing device with a single fragrance dispenser.

FIG. 4 shows a preferred atomizer for use in our invention. As shown in FIG. 4, a piezoelectrically actuated atomization device 70 generally comprises an atomizer assembly 34, which includes an orifice plate 37, and a replaceable reservoir assembly 80. The reservoir assembly 80 includes a reservoir 31 containing fluid and a wick 107. When one reservoir assembly 80 is removed by a user and replaced with another reservoir assembly, the wick 107 instantaneously delivers fluid to the orifice plate 37.

The atomization device 70 comprises a housing 72 formed as a hollow plastic shell. A horizontal platform 25 extends across the interior of the housing 72. A battery 76 is supported by means of support prongs 25a which extend down from the underside of the platform 25 inside the housing 72. In addition, a printed circuit board 28 is supported on support elements 25b, which extend upwardly from the platform 25. A liquid reservoir assembly 80 is replaceably mounted to the underside of a dome-like formation 25c on the platform 25.

The liquid reservoir assembly 80 comprises a liquid reservoir 31 for holding a liquid to be atomized, a plug 33, which closes the top of the reservoir, and the wick 107, which extends from within the liquid reservoir 31 through the plug 33, to a location above the liquid reservoir 31. The plug 33 is constructed to allow removal and replacement of the complete liquid reservoir assembly 80 from the underside of the dome-like formation 25c on the platform 25. Preferably, the plug 33 and the platform are formed with a bayonet attachment (not shown) for this purpose. When the replaceable liquid reservoir assembly 80 is mounted on the platform 25, the wick 107 extends up through a center opening in the dome-like formation 25c. The wick 107, operates by capillary action to deliver liquid from within the liquid reservoir 31 to a location just above the dome-like formation 25c on the platform 25.

An atomizer assembly 34 is supported on the platform 25 in cantilever fashion by means of a resilient, elongated wire-like support 77. As is described more fully in copending U.S. patent application Ser. No. 10/304,215, filed Nov. 26, 2002, assigned to the assignee of this invention, in the preferred embodiment, the wire-like support 77 is attached at its ends to posts, which protrude upward from the platform 25. The support 77 is shaped such that it resiliently supports the lower surface of the orifice plate 37 and a spring housing 39, while a spring 43 resiliently presses on the upper surface of an actuator element 35. Together, the support 77 and the spring 43 hold the orifice plate 37 in place in a manner that allows the orifice plate 37 to move up and down against the resilient bias of the wire-like support 77.

The atomizer assembly 34 comprises an annularly shaped piezoelectric actuator element 35 and the circular orifice plate 37, which extends across and is soldered or otherwise affixed to the actuator element 35. A construction of a vibrator-type atomizer assembly is known and is described, for example, in U.S. Pat. No. 6,296,196, which is incorporated herein by reference. Accordingly, the atomizer assembly 34 will not be described in detail except to say that when alternating voltages are applied to the opposite upper and lower sides of the actuator element 35, these voltages produce electrical fields across the actuator element and cause it to expand and to contract in radial directions. This expansion and contraction is communicated to the orifice plate 37 causing it to flex so that a center region thereof vibrates up and down. The center region of the orifice plate 37 is domed slightly upward to provide stiffness and to enhance atomization. The center region is also formed with a plurality of minute orifices which extend through the orifice plate 37 from the lower or under surface of the orifice plate 37 to its upper surface. A flange is provided around the center region of the dome.

Figure 9:
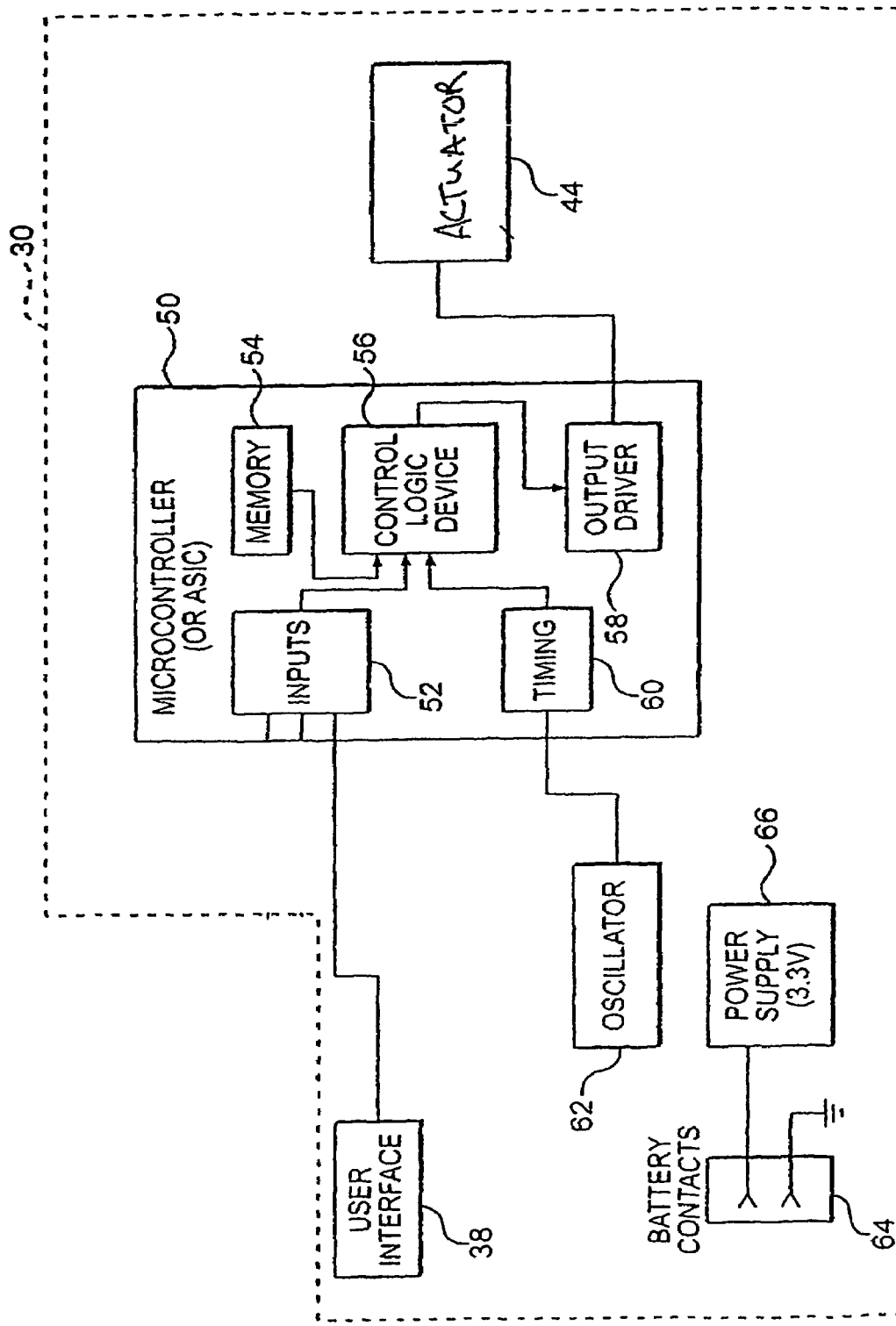
FIG. 9 is a circuit diagram of controls for operating a fragrance dispensing device according to our invention.

In operation, the battery 76 supplies electrical power to circuits on the printed circuit board 28 and these circuits convert this power to high frequency alternating voltages. (Of course, in other embodiments, power may be provided by an AC power supply, by wired connection to a controller 30, discussed below, or by other conventional means.) A suitable circuit for producing these voltages is shown and described in U.S. Pat. No. 6,296,196, noted above. As described in that patent, the device may be operated during successive on and off times. The successive on and off times provide intermittent "puffs" of fragrance. The on and off times may be controlled by a preset program, a user interface working through a processor, or by the logic of controller 30. To achieve this end, the atomizer device 70 includes interface 98 and controller 30 (shown in FIG. 9), which communicate through the transmission of signals through a direct connection via a wire, or through a wireless transmission with the controller 30. The system can involve one way communication to the controller 30, or two-way communication when the interface has a display or the like for providing information to a user. A keypad may also be provided to allow user input. The atomization control device 70 may also be provided with suitable sensors and circuitry for generating signals based on the sensed information, such as the need to refill/replace a reservoir 31 or light conditions (in which case suitable sensors would be provided.) Such modifications would be readily understood by one of ordinary skill in the art.

Figure 5:
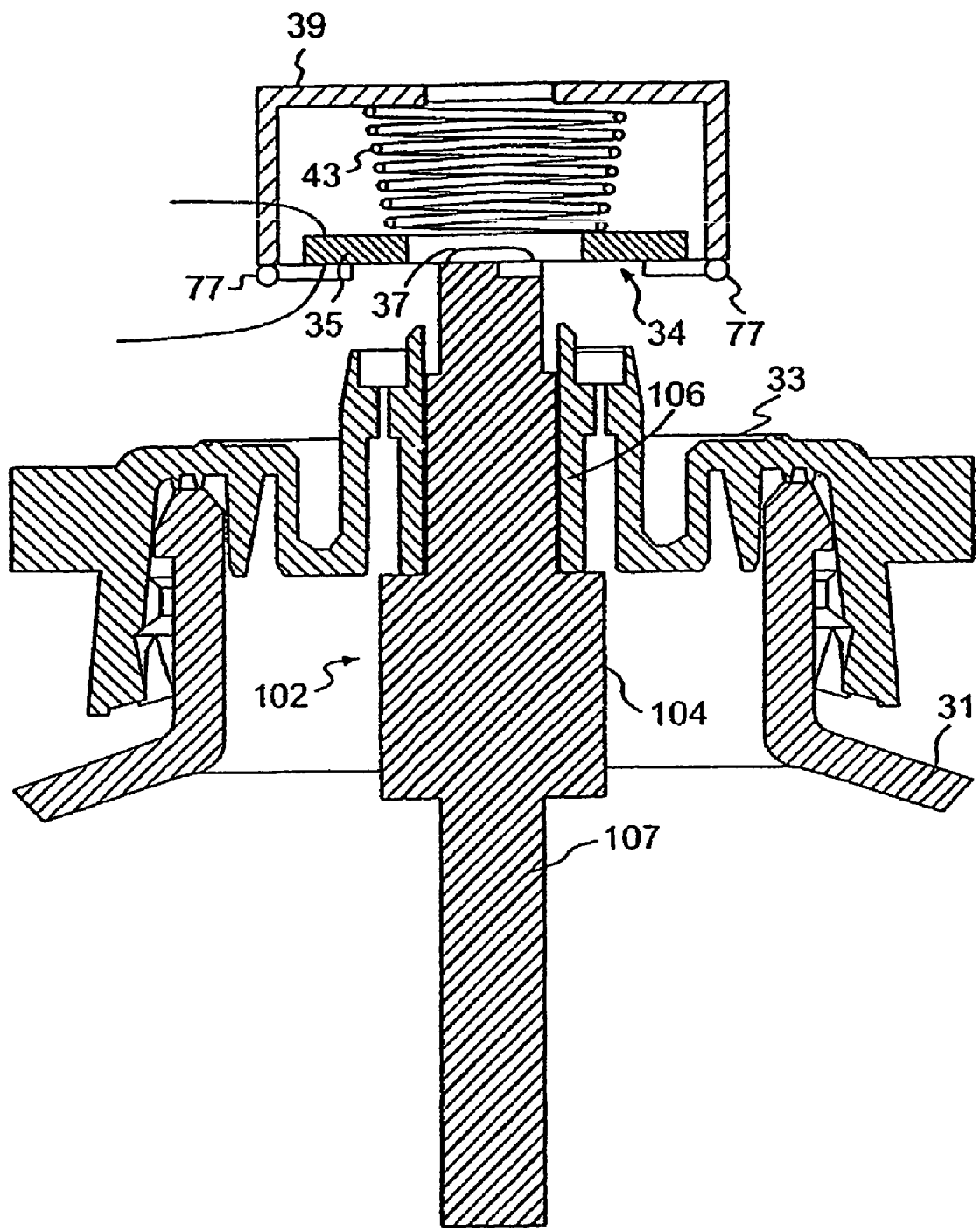
FIG. 5 is a cross-sectional view of an atomization assembly used in the fragrance dispenser shown in FIG. 4.

When the atomizer assembly 34 is supported by the support member 77, the flange of the orifice plate 37 is positioned in contact with the upper end of the wick 107. The atomizer assembly 34 is thereby supported above the liquid reservoir assembly 80 such that the upper end of the wick 107 touches the underside of the orifice plate 37, as shown in FIG. 5. Thus, the wick 107 delivers liquid from within the liquid reservoir 31 by capillary action to the underside of the orifice plate 37, which upon vibration, causes the liquid to pass through its orifices and be ejected from its opposite side (i.e., the upper surface) in the form of very small droplets.

It will be appreciated from the foregoing that the horizontal platform 25 serves as a common structural support for both the liquid reservoir assembly 80 and the atomizer assembly 34. Thus, the horizontal platform maintains the liquid reservoir assembly 80, and particularly, the upper end of the wick 107, in alignment with the orifice plate 37 of the atomizer assembly 34. Moreover, because the atomizer assembly 34 and the orifice plate 37 are resiliently mounted, the upper end of the wick 107 will press against the under surface of the orifice plate 37 and/or the actuator element 35 irrespective of dimensional variations which may occur due to manufacturing tolerances when one liquid reservoir is replaced by another. This is because if wick 107 of the replacement liquid reservoir assembly 80 is higher or lower than the wick 107 of the original liquid reservoir assembly 80, the action of the spring 43 will allow the orifice plate 37 to move up and down according to the location of the wick 107 in the replacement reservoir assembly 80, so that the wick 107 will always press against the underside of the orifice plate 37 and/or the actuator element 35. It is preferable that the wick 107 be of a substantially solid, dimensionally stable material so that it will not become overly deformed when pressed against the underside of the resiliently supported orifice plate 37.

As can be seen in FIG. 5, the wick 107 extends from inside the liquid reservoir 31 up through the plug 33 in the top of the reservoir 31 to contact the orifice plate 37 and/or the actuator element 35 from near the bottom of the liquid reservoir 31. The wick 107 has longitudinally extending capillary passages which draw liquid up from within the reservoir 31 to the upper end of the wick 107.

The wick 107 preferably includes an integrally formed attachment assembly for securing the wick 107 to the plug 33. Of course, the attachment assembly may be a separate piece affixed to the wick 107. The attachment assembly includes a collar 102 having a lower segment 104 of a relatively large diameter and an upper segment 106 of a relatively small diameter. The top of the lower segment 104 contacts the plug 33 to prevent the wick 107 from moving out of the reservoir 31. The upper segment 106 frictionally fits into the aperture in the plug 33.

As also can be seen in FIG. 5, the upper end of the wick 107 enters into an opening in the bottom of the spring housing 39 to supply liquid to a location just below or on the bottom surface of the orifice plate 37. The wick 107 may be substantially in contact with a flange portion on the periphery of the domed portion of the orifice plate 37, or the actuator element 35. However, the wick 107 may include a top surface having different levels so that a portion of the wick 107 is not in contact with the orifice plate 37 or the actuator element 35.

Again, other atomization devices may be substituted as desired in consideration of design choices, manufacturing costs, etc. Also, a more detailed explanation of the atomization device 70 may be found in copending U.S. patent application Ser. No. 10/412,911, filed Apr. 14, 2003. Also, an atomization device is only one type of dispenser that may be used, and others may be substituted in view of design considerations.

Operational Controls

FIG. 7 shows a circuit diagram for one possible arrangement of components for a controller 30 for controlling a fragrance dispenser such as that shown in FIGS. 6-8, as well as connected items. In this embodiment, the controller 30 is powered by a battery (not shown) through battery contacts 64; however, other sources of power, such as an AC current source, may also be used. A power supply 66 draws power from the battery through the battery contacts 64 and then supplies 3.3 volts to the controller 30. In other embodiments, the current level (or voltage level) used may be altered as desired or necessary for the components to be powered.

The microcontroller or (ASIC) 50 controls the operation of the controller 30, and is powered by power supply 66. (The power supply 66 may also power the sensor(s) and dispensers, if a wired connection is provided among these items. Alternatively, each different item may have its own power supply means.) The microcontroller 50 includes a control logic device 56 that provides the operational instructions to the various dispensers in accordance with input signals or internal programs. The input signals may be signals from a user interface 38. The user interface may be levers or knobs (as shown in FIG. 6), keypads, or other known interfaces, depending on the needs of the system and relative complexity of the user control to be offered. The interface 38 sends input signals to inputs 52. The inputs 52 transfer the signals to the control logic device 56. Further, memory 54 is provided to store programs that may also provide signals to the control logic device 56, on their own, or in cooperation with other signals.

Having received one or more signals from the user interface 38, memory 54, external input, a sensor, or a combination thereof, the control logic device 56 sends a signal for controlling the operation of the array of dispensers to output driver 58. Preferably, pulse width modulation is used to drive and to control the dispensers, and the output driver 58 sets the duty cycles for the operation of the dispensers based on the instructions from the control logic device 56. Thus configured, the duty cycles can be used to control the frequency of bursts of emission of fragrances to adjust the rate at which the corresponding fragrances are dispensed, and thus, the potency of each substance in the air. In preferred embodiments, a burst or puff of fragrance is emitted every 9-36 seconds, with the burst itself arising from the operation of the actuator for a period of about 11 msec. Of course, when dispensers other than piezoelectrically actuated atomization devices emitting chemicals are used, the control signals may be made to provide suitable control for the specific device. Also, pulse width modulation is only one control mechanism, and other signal forms may be used by the output driver 58.

The microcontroller 50 may also include a timing mechanism 60 and an oscillator 62. The timing mechanism 60 and oscillator 62 control the operation of microcontroller 50 in accordance with the set program or other settings from the sensor 26, user interface 38, and/or memory 54.

As discussed, this is only one arrangement for the controller 30. As would be understood by one of ordinary skill in the art, other arrangements are possible for the controller 30.

The control signals may be provided to the various dispensers through a direct connection from wires, in which case, the control signals may be in the form of voltages or coded pulses (or other coded signals). In such a case, the coded signals may be provided with appropriate addresses to ensure that they are recognized only by the particular dispenser to which they are directed. Other conventional means may also be used.

PREFERRED EMBODIMENTS

Figure 10:
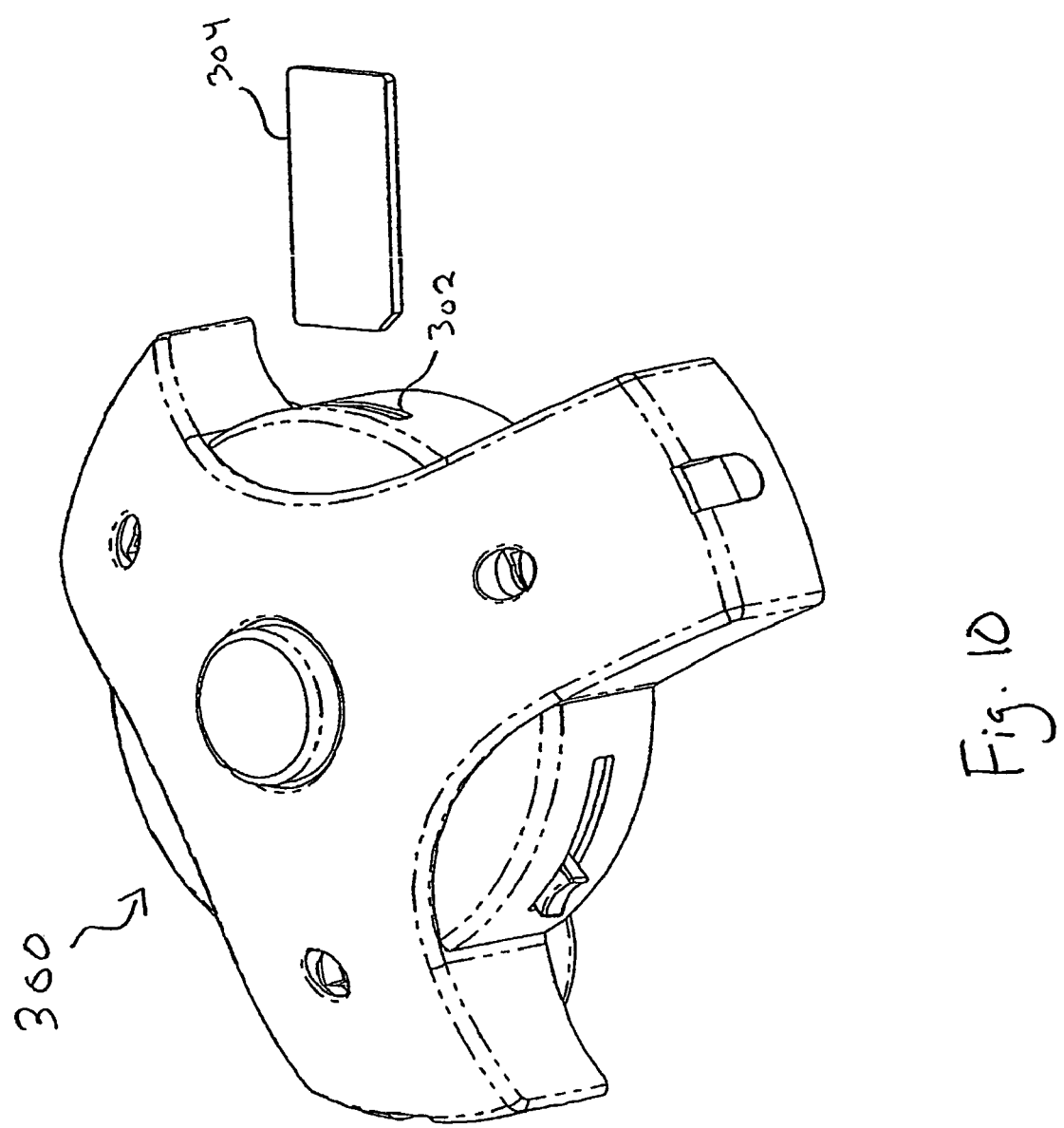
FIG. 10 is a perspective view of another embodiment of a fragrance dispensing device according to our invention.

As discussed above, instructions may also be provided to the microcontroller 50 from locations other than, or in addition to, memory 54. FIGS. 10 and 11 show another embodiment of our invention in which a fragrance dispensing system 300 with multiple fragrance dispensers is operated, at least partially, from programs provided from a memory other than internal memory 54, shown in FIG. 9. Fragrance dispensing system 300 works in a manner similar to fragrance dispensing systems described above, but further includes a card slot 302. Card slot 302 is adapted to receive a memory card 304. Card slot 302 comprises a card reading device 306 which reads information stored on card 304. That information may be control programs, ID information, or other information that relates to controlling the microprocessor, at least partially.

Any one of a number of conventional means may be used for the combination of the card slot and memory card. Preferably, however, memory card 304 is a Smart Card (containing a flash memory), the contents of which are read by the reading device 306 of card slot 302.

Memory card 304 stores therein computer-readable instructions for controlling the processor which controls the emission of the different fragrances from a plurality of fragrance reservoirs stored therein.

Thus, rather than operational programs being read from a memory or programmed by a user, the card 304 can provide a set program for operating the dispensing system, or multiple programs from which a user may choose. Alternatively, the card may provide information relating to a program stored in an internal memory, so that a combination of internal and external information is used.

In particular, a program stored in memory card 304 may indicate when different fragrances are to be emitted, concentrations thereof, or set programs of coordinated emission of different fragrances independently over time (or specified, simultaneous combinations of fragrances to produce an overall effect). In particular, card 304 may be designed for use with a specific group of different, but related, fragrances. In preferred embodiments, the different fragrances are selected from a group having a common theme. Thus, a card 304 is designated for use with one or more indicated combinations of fragrances. For instance, a card 304 can provide various programs for the use of multiple citrus scents (e.g., lime, lemon and tangerine), so as to specify programs to coordinate the emission thereof. Alternatively, the same card can control specific combinations of citrus scents or specific combinations of, for example, woodland scents, with the programs in a given card being usable for either grouping in an effective manner.

A user may be instructed by printed instruction manuals, a graphical interface or otherwise, as to which combinations may be used with a particular card (or vice or versa) as well as which position at which different fragrance reservoirs are to be loaded in the dispensing system, to ensure that the programs control emission properly. Indicia may be provided at different loading positions in a dispensing system, to help the user load the reservoirs. (In other embodiments, a reading device can read information from the reservoirs to determine the fragrance contained therein, so that the microcontroller can coordinate the emission of the proper fragrances in accordance with a program, based on the detected positions and corresponding atomizers.)

With such a system, manufacturers can sell packages having a combination of fragrances (i.e., three citrus scents) with a card for providing preferred programs for operating a dispensing system when those citrus scents are loaded therein. This provides a beneficial marketing system that allows multiple scents to be sold together, while providing a user with an easy and effective way of managing the emission of the different fragrances. Alternatively, the scents and memory cards can be sold separately, in which case, the packaging for those different items may indicate which combinations of fragrances are preferred for use with particular memory cards or the manner in which the fragrance reservoirs are to be loaded in a device. Thus, as new scents or scent themes, and emission techniques are developed, the dispensing device can adapt to operate at optimum performance levels and with preferred programs of operation, which would perhaps otherwise be difficult for a user to program on his or her own.

While the preferred embodiment uses a memory card that electronically stores the computer-readable programs, other cards are possible. For instance, the cards may simply have program information printed thereon (such as a bar code or other readable instructions), and the reading device 306 may be an optical scanner that optically reads information from the card once inserted in slot 302. Also, although the term "card" is used herein, the memory card may be of any one of a number of configurations, and not merely card-shaped. A memory card can be understood to be any device that may be mated with the fragrance dispensing system to provide information thereto, which information instructs, partially or wholly, the operation of the system (e.g., microcontroller/microprocessor) to dispense fragrance(s).

In another embodiment of our invention, the reservoir 31 may be configured to store, on its own, information used in instructing the microprocessor (or microcontroller 50) to control emission from one or more of the reservoirs 31. Thus, instead of a separate memory card being provided for use with multiple reservoirs, instructions or other information may be provided integrally with each reservoir 31. Such information may be provided on a chip (which may comprise a flash memory or other such computer-readable memory devices such as an RF ID tag) or an informational display provided on the reservoir 31. As shown in FIG. 12, a reservoir 31 has a memory 404 mounted on its plug/neck. The fragrance dispensing device 400 includes a memory reading device 402, which reads the information stored on memory 404 when reservoir 31 is loaded in the fragrance dispensing device 400. In this embodiment, the reading device 402 is an RF ID tag that reads computer-readable programs which are stored in memory 404.

Alternatively, when the information or instructions are displayed on reservoir 31, fragrance dispensing device 400 may include an optical scanner that reads bar codes or other information displayed on the reservoir 31.

The memory or indicia displayed on the reservoir 31 may include information relating to the specific type of fragrance stored in the reservoir 31, the family of fragrances to which the fragrance stored in the reservoir 31 belongs, preferred operational settings for the fragrance, preferred programs of independent operation for the fragrance, preferred programs of operation when used in conjunction with other types of fragrances, etc. For instance, the information can indicate specific duty cycles to be used in controlling the emission of the fragrance, so as to set a preferable concentration (e.g., puff rate) for that specific fragrance. More specifically, the information can indicate that, in a preferred setting, an actuator element causes the emission of fragrance for a period of 11 msec. every eleven seconds, for example. The information can also indicate a program for operating the emission of the fragrance so as to vary the concentration based on the times of day or in patterns to prevent desensitization to the fragrance. The information may also include instructions for emitting the fragrance from the reservoir 31 in a set pattern in combination with fragrances from other reservoirs stored in fragrance dispensing device 400.

In operation, reading device 402 reads information from the reservoir 31, for instance, from memory 404 mounted thereon or from indicia displayed thereon. The reading device then sends signals relating to the read information to the microprocessor. The microprocessor controls the operation of the dispensing device 400 to control emission of fragrances from the different fragrance reservoirs 31 based on the signals. For instance, the microprocessor might automatically activate emission of a fragrance from a reservoir 31 based on instructions read from that reservoir 31 or may set various modes of operation based on the information, which modes may be selected by the user. For instance, as shown in FIG. 6, a mode selector 212 may allow a user to select different modes of operation, with those modes being determined based on information read from reservoirs 31. Thus, the dispensing device 400 personalizes the mode settings based on the types of fragrance or the family of the fragrance(s) loaded in the device.

When the read information relates to not only the particular fragrance stored in a reservoir 31, but also the manner in which that fragrance may be combined with other types of fragrances, the microprocessor can detect whether those other fragrances are loaded into the system, and offer programs based on those combinations, if the necessary fragrances are available. The microprocessor may detect this information by providing unique addresses for the different positions into which reservoirs 31 are loaded, so as to control the proper fragrance at the proper time and/or concentration in accordance with the program. Of course, other means may be used to identify the respective locations of the different fragrance reservoirs 31, other than addressing each location and reading device associated therewith.

With such a configuration, a user can choose different modes based on the identification of the fragrances or instructions included with the different reservoirs using selector switches, as shown in FIG. 6. Alternatively, a more complex user interface may be provided with a key pad and display, for instance, to allow a user to choose from and program a wider range of control settings.

When the reservoirs just contain information referring to the identity of the fragrance contained in that reservoir 31, there may be a memory provided with the microprocessor 403 storing set programs that correspond to different fragrance IDs.

FIG. 13 shows yet another embodiment of our invention in which multiple knobs 210 are provided on a fragrance dispensing system 500. Knobs 210a-c are similar to the knob 210 described with respect to FIG. 6, inasmuch as they control the intensity level of the fragrance(s). However, instead of a single knob 210 for controlling the overall level of the fragrance emission, multiple knobs are provided to allow the user to adjust emission from different fragrance reservoirs independently. Thus, in addition to selecting a specific mode using a mode selection lever 212, a user may independently adjust different fragrances being used in the emission program, to tailor the emission to his or her particular preferences. Independent control knobs 210a-c may be combined in any one of the above-discussed embodiments, to allow for additional user control.

Also, with dispensers according to our invention, unique combinations of fragrances, and methods of providing the same are possible, as generally described above. More specifically, with a device mounting multiple reservoirs 31, the different reservoirs may be individually selected by a user based on his or her preferences, or groups of reservoirs may be sold in combination packages. When combination packages are sold, it is preferable that the different reservoirs include fragrances from a single family. For instance, when a package of three reservoirs is sold, each different reservoir may include a different citrus scent—lemon, lime and tangerine, for example.

When fragrance reservoirs from a commonly-themed family are used, the microprocessor may be programmed to control an emission program in which the different fragrances are alternately emitted, independently, for set periods of time. For instance, a lemon fragrance may be emitted in short, consecutive (but intermittent) bursts for a period of five minutes, followed by short, consecutive (but intermittent) bursts of a lime fragrance for a period of five minutes, followed by short consecutive (but intermittent) bursts of a tangerine fragrance for a period of five minutes. These five-minute periods (or other length periods) may be repeated, as set by a program. With other programs, the alternating periods may include set combinations of the fragrances for set periods. For instance, there may be five minutes of a combination of lemon and lime fragrances emitted, followed by five minutes of emission of a combination of lime and tangerine, followed by five minutes of a combination of tangerine and lemon. Also, the concentration of one fragrance can be varied. Other combinations are, of course, possible. Further, bursts of fragrance are not necessary, but preferred when using a piezo-type dispenser.

With these alternating emissions of similarly themed fragrances (or combinations thereof), fragrance fatigue by users can be avoided. Specifically, it has been found that olfactory response by a user can become desensitized if the same fragrance is continually emitted. While the use of short, spaced-apart bursts of emission can reduce fragrance fatigue (otherwise known as a temporary anosmia), some fragrance fatigue is possible even when using such spaced-apart bursts of fragrance. By alternating the use of similarly themed fragrances over consecutive set periods of time, fragrance fatigue can be further diminished so that a user does not become desensitized to the fragrances being emitted by the device. This leads to a more fragrant and pleasant environment for the users. Of course, the fragrances do not have to be selected from a common theme of fragrances, but doing so may provide for a more pleasant experience.

This effect may also be achieved by varying not only the contents of particular combinations of similarly theme fragrances (e.g., lemon and lime as opposed to lime and tangerine), but also the respective concentration levels of the combinations. For instance, lemon and lime scents can be used in combination, with one being provided in greater concentration than the other for a set period of time, and then switching the relative concentration levels for a following period of time. These alternating concentrations can also be repeated to refresh olfactory senses and provide a more pleasant experience. Further, varying concentration levels of a single fragrance may also be used.

These embodiments, however, are only examples of different means for implementing our invention. One of ordinary skill in the art would understand that any number of combinations of the features discussed above, or equivalent features, may be used to achieve systems and methods in accordance with our invention. Accordingly, broad interpretation is to be afforded to our invention, as described in the claims set forth below.

INDUSTRIAL APPLICABILITY

This invention make possible an area condition control wherein a region can be provided with multiple fragrances in a coordinated manner, thereby to achieve an overall desired effect in the condition of the area.

We claim:

1. A volatile substance dispensing system comprising:
a plurality of electromechanical volatile substance dispensers, each configured to emit a volatile substance from a replaceable volatile substance reservoir when the reservoir is loaded in the dispensing system so as to communicate the volatile substance to each respective dispenser;
a programmable microprocessor for controlling the emission of different volatile substances From the plurality of dispensers;
a memory card reading device for reading program in Formation from a replaceable memory card, wherein the replaceable memory card comprises information relating to one or more set programs for instructing the microprocessor to control volatile substance emission from the plurality of dispensers in a coordinated manner; and
a user interface that includes at least one knob disposed on a housing of the dispensing system that allows a user to instruct the microprocessor to control the volatile substance emission according to the one or more set programs.

2. A volatile substance dispensing system according to claim 1, wherein the dispensing system further includes a continuous action air freshener.

3. A volatile substance dispensing system according to claim 1, wherein the volatile substance is selected from the group consisting of fragrance, insect repellant, insecticide, disinfectant, sanitizer, and water.

4. A volatile substance dispensing system according to claim 1, further comprising a sensor for sensing at least one of light intensity, airborne chemicals, humidity, sound, motion, and temperature, wherein the microprocessor controls the emission of the volatile substances at least partially based on information relating to a sensed condition output from the sensor.

5. A volatile substance dispensing system according to claim 1, further comprising a user interface that comprises a mode lever to enable a user to switch between the one or more programs to control the volatile substance emission from one or more of the plurality of electromechanical volatile substance dispensers.

6. A volatile substance dispensing system according to claim 1, wherein the memory card is a flash memory device.

7. A volatile substance dispensing system according to claim 1, wherein the memory card reading device is an optical scanner that reads information displayed on the memory card.

8. A method of selling replaceable volatile substance reservoirs for use in a volatile substance dispensing device which is configured to mount a plurality of volatile substance reservoirs simultaneously and to operate electromechanical dispensers to emit volatile substances from respective volatile substance reservoirs independently or in combination, the dispensing device having a microprocessor and a memory card reading device for reading a memory card containing information relating to one or more programs for instructing the microprocessor to control emission of volatile substances from the volatile substance reservoirs in accordance with the one or more programs, the method comprising:
  grouping a plurality of volatile substance reservoirs, each having a different volatile substance;
  storing on a memory card information relating to one or more set programs for instructing the microprocessor to control the emission of the different volatile substances from the group of volatile substance reservoirs;
  providing a user interface that includes at least one knob disposed on a housing of the dispensing device that allows a user to instruct the microprocessor to control the emission of the different volatile substances according to the one or more set programs;
  packaging the plurality of volatile substance reservoirs together with the memory card; and
  offering the packaged materials for sale as a single item.

9. The method according to claim 8, wherein the memory card comprises a flash memory.

10. The method according to claim 8, wherein the memory card has the information relating to the one or more computer-readable programs printed thereon.

11. The method according to claim 8, wherein the volatile substances are selected from the group consisting of fragrance, insect repellant, insecticide, disinfectant, sanitizer, and water.

12. A volatile substance dispensing system comprising:
  a plurality of volatile substance dispensers configured to dispense volatile substances from a plurality of replaceable volatile substance reservoirs, respectively, when the plurality of volatile substance reservoirs are loaded in the dispensing system so as to communicate a volatile substance to each respective dispenser;
  a microprocessor for controlling the plurality of volatile substance dispensers to emit volatile substances from the plurality of volatile substance reservoirs according to one or more set programs; and
  a user interface that includes a mode lever to enable a user to instruct the plurality of volatile substance dispensers to dispense the volatile substances from the respective plurality of replaceable volatile substance reservoirs according to the one or more set programs, wherein the microprocessor controls the plurality of volatile substance dispensers to perform at least one of (i) repetitive alternation between independent emissions of different volatile substances, (ii) repetitive alternation between emissions of different combinations of volatile substances, or (iii) repetitive alternation between different emission intensifies of at least one volatile substance, in a set pattern;
  wherein the microprocessor controls the plurality of volatile substance dispensers to emit repeatedly (i) intermittent bursts of a first combination of volatile substances from different reservoirs over a first period of time, and (ii) intermittent bursts of a second combination of volatile substances from different reservoirs over a second period of time.

13. A volatile substance dispensing system according to claim 12, wherein the dispensing system further includes a continuous action air freshener.

14. A volatile substance dispensing system according to claim 12, wherein the volatile substance is selected from the group consisting of fragrance, insect repellant, insecticide, disinfectant, sanitizer, and water.

15. A volatile substance dispensing system according to claim 12, wherein the volatile substance is a fragrance, and the set pattern reduces fragrance fatigue by a user.

16. A volatile substance dispensing system according to claim 12, further comprising a sensor for sensing at least one of light intensity, airborne chemicals, humidity, sound, motion, and temperature, wherein the microprocessor controls the emission of the volatile substances at least partially based on information relating to a sensed condition output from the sensor.

17. A volatile substance dispensing system according to claim 12, wherein the user interface allows a user to switch between different emission modes.

18. A volatile substance dispensing system according to claim 12, wherein the microprocessor controls the plurality of volatile substance dispensers (i) to emit intermittent bursts of a first volatile substance over a first period of time, (ii) to emit intermittent bursts of a second volatile substance over a second period of time following the first period of time, and (iii) to repeat the first and second periods.

19. A volatile substance dispensing system according to claim 12, wherein the microprocessor controls the plurality of volatile substance dispensers to emit repeatedly (i) intermittent bursts of a combination of volatile substances from different reservoirs over a first period of time, and (ii) intermittent bursts of a single volatile substance from one reservoir over a second period of time.

20. A volatile substance dispensing system comprising:
  a plurality of electromechanical volatile substance dispensers, each configured to dispense a volatile substance from a different replaceable volatile substance reservoir, each reservoir comprising a wick that (i) extends into the reservoir, and (ii) communicates the volatile substance from the reservoir through capillary action, to deliver the volatile substance to the electromechanical volatile substance dispenser, wherein each electromechanical volatile substance dispenser comprises:
  (a) an orifice plate; and
  (b) a piezoelectric actuator element that expands and contracts when alternating voltages are applied thereto, which expansion and contraction is communicated to the orifice plate to cause the orifice plate to vibrate and, consequently, to eject into the air droplets of a volatile substance communicated by the wick;
  a microprocessor for controlling an emission of volatile substances from the plurality of electromechanical volatile substance dispensers based on one or more set programs by independently controlling the voltage applied to each actuator element; and
  a plurality of knobs disposed on a housing of the volatile substance dispensing system, wherein each knob is independently associated with one of the plurality of electromechanical volatile substance dispensers to allow independent adjustment of a level of the emission of the volatile substance from each of the plurality of electromechanical volatile substance dispensers according to the one or more set programs.

21. A volatile substance dispensing system according to claim 20, wherein the dispensing system further includes a continuous action air freshener.

22. A volatile substance dispensing system according to claim 20, wherein the volatile substance is selected from the group consisting of fragrance, insect repellant, insecticide, disinfectant, sanitizer, and water.

23. A volatile substance dispensing system according to claim 20, further comprising a sensor for sensing at least one of light intensity, airborne chemicals, humidity, sound, motion, and temperature, wherein the microprocessor controls the emission of the volatile substances at least partially based on information relating to a sensed condition output from the sensor.

24. A volatile substance dispensing system according to claim 20, further comprising a mode lever to enable a user to switch between different programs for controlling the emission of the volatile substances from the plurality of electro-mechanical volatile substance dispensers.

25. A volatile substance dispensing system comprising:
   at least one dispenser configured to dispense a volatile substance from a plurality of replaceable volatile substance reservoirs, when the plurality of replaceable volatile substance reservoirs are loaded in the volatile substance dispensing system so as to communicate a volatile substance to the at least one dispenser, the plurality of replaceable volatile substance reservoirs including information relating to one or more computer-readable programs from which a user may choose;
   at least one reading device the reading the information from the plurality of replaceable volatile substance reservoirs;
   a microprocessor for receiving signals from the reading device relating to the information and controlling the at least one dispenser to emit volatile substance from the plurality of replaceable volatile substance reservoirs in accordance with the signals communicated from the reading device;
   a knob disposed on a housing of the volatile substance dispensing system for controlling a level of volatile substance emission from the plurality of replaceable volatile substance reservoirs;
   a mode lever to manually switch between the one or more computer-readable programs for controlling the level of the volatile substance emission from the plurality of replaceable volatile substance reservoirs; and
   wherein the housing secures the at least one dispenser, and the replaceable volatile substance reservoirs are mounted within the housing so as to communicate volatile substances to the dispenser when loaded in the volatile substance dispensing system.

26. A volatile substance dispensing system according to claim 25, further comprising selection means for selecting one of the control programs to be run by the microprocessor when more than one program is read from the plurality of replaceable volatile substance reservoirs.

27. A volatile substance dispensing system according to claim 25, wherein the reading device reads a flash memory integrated with the plurality of replaceable volatile substance reservoirs, which stores the information relating to the one or more of the computer-readable control programs.

28. A volatile substance dispensing system according to claim 25, further comprising:
   a plurality of dispensers, each configured to dispense a volatile substance from a respective, replaceable volatile substance reservoir when the volatile substance reservoir is loaded in the volatile substance dispensing system, each volatile substance reservoir including information relating to one or more computer-readable programs; and
   a plurality of reading devices for reading the information from each of the respective reservoirs, wherein the microprocessor receives signals from the plurality of reading devices relating to the one or more computer-readable programs from the volatile substance reservoirs and controls the dispensers to emit volatile substance based on the signals from the reading devices.

29. A volatile substance dispensing system according to claim 28, wherein the microprocessor controls the plurality of dispensers to emit a coordinated combination of volatile substances from respective reservoirs based on the received signals.

30. A volatile substance dispensing system according to claim 25, wherein the dispensing system further includes a continuous action air freshener.

31. A volatile substance dispensing system according to claim 25, wherein the volatile substance is selected from the group consisting or fragrance, insect repellant, insecticide, disinfectant, sanitizer, and water.

32. A volatile substance dispensing system according to claim 25, further comprising a sensor for sensing at least one of light intensity, airborne chemicals, humidity, sound, motion, and temperature, wherein the microprocessor controls the emission of a volatile substance at least partially based on information relating to a sensed condition output from the sensor.

33. A volatile substance dispensing system according to claim 25, further comprising a user interface, wherein the user interface allows a user to instruct the microprocessor to control the emission of a volatile substance.

* * * * *

UNITED STATES PATENT AND TRADEMARK OFFICE
CERTIFICATE OF CORRECTION

| | | |
|---|---|---|
| PATENT NO. | : 7,610,118 B2 | Page 1 of 1 |
| APPLICATION NO. | : 10/549435 | |
| DATED | : October 27, 2009 | |
| INVENTOR(S) | : Heather R. Schramm et al. | |

It is certified that error appears in the above-identified patent and that said Letters Patent is hereby corrected as shown below:

Column 14, Line 32 Claim 1: replace "From" with --from--

Column 14, Line 34-35 Claim 1: replace "in Formation" with --information--

Column 15, Line 62 Claim 12: replace "intensifies" with --intensities--

Column 17, Line 30 Claim 25: replace "the" with --for--

Signed and Sealed this

Third Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,610,118 B2
APPLICATION NO. : 10/549435
DATED : October 27, 2009
INVENTOR(S) : Schramm et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this

Twelfth Day of October, 2010

David J. Kappos
*Director of the United States Patent and Trademark Office*